United States Patent [19]

Zardi

[11] 4,372,920

[45] Feb. 8, 1983

[54] AXIAL-RADIAL REACTOR FOR HETEROGENEOUS SYNTHESIS

[75] Inventor: Umberto Zardi, Lugano, Switzerland

[73] Assignee: Ammonia Casale S.A., Lugano, Switzerland; a part interest

[21] Appl. No.: 162,436

[22] Filed: Jun. 24, 1980

[30] Foreign Application Priority Data

Jul. 13, 1979 [IT] Italy .............................. 24334 A/79
Jun. 11, 1980 [IT] Italy .............................. 22701 A/80

[51] Int. Cl.$^3$ .......................... B01J 8/04; C01C 1/04
[52] U.S. Cl. .................................. 422/148; 422/191; 422/192; 422/194; 422/195; 422/218
[58] Field of Search ............... 422/148, 191, 192, 218, 422/194, 195, 181

[56] References Cited

U.S. PATENT DOCUMENTS

| | | | |
|---|---|---|---|
| 2,475,855 | 7/1949 | Peters | 422/192 |
| 2,646,391 | 7/1953 | Houdry | 422/191 X |
| 2,887,365 | 5/1959 | De Rycker et al. | 422/148 X |
| 3,932,139 | 1/1976 | Vilceana et al. | 422/148 X |
| 4,152,407 | 5/1979 | Fuchs | 422/148 X |
| 4,205,044 | 5/1980 | Gramotica | 422/192 |
| 4,277,444 | 7/1981 | Landeghem | 422/192 |

Primary Examiner—Michael S. Marcus
Attorney, Agent, or Firm—Holman & Stern

[57] ABSTRACT

Disclosed is a reactor for heterogeneous catalytic reactions of gaseous reactants under pressure, comprising: a container having an inlet for introduction of gaseous reactants and an outlet for the efflux of products of the reactions; a cartridge having a cylindrically shaped wall placed within the container and communicating with the inlet and the outlet; at least two stationary-bed, catalyst-containing baskets supported within the cartridge, each of the baskets including an imperforate bottom section, a cylindrical outer perforated wall, a cylindrical inner concentric perforated wall and an annular opening defined by the inner and outer perforated walls in the upper end of each stationary-bed, catalyst-containing basket, the opening formed in a plane approximately perpendicular to the longitudinal axis of the inner and outer perforated walls, the bottom section and the inner and outer perforated walls cooperating with the cylindrically shaped cartridge wall to form a partially restrictive axial flow means, whereby a portion of the gaseous reactants enters or departs and passes through the annular opening in each of the stationary-bed, catalyst-containing baskets substantially in the axial direction and the remainder of the gaseous reactants enters and passes through the cylindrical outer perforated wall of each of the catalyst-containing baskets substantially in the radial direction.

23 Claims, 10 Drawing Figures

AXIAL-RADIAL REACTOR FOR HETEROGENEOUS SYNTHESIS

BACKGROUND OF THE INVENTION

1. Field of Invention

This invention concerns a reactor for heterogeneous synthesis under pressure, and more particularly for the catalytic synthesis of ammonia (from nitrogen and hydrogen) and methanol (from carbon monoxide and hydrogen), said reactor involving the use of a granular catalyst (in various shapes and with different specifications) arranged in one or more superimposed layers, with the gas running through each layer in a first zone with a prevalently axial flow and in a second zone with a prevalently radial flow (down-flow axial-radial reactor with gas running downwards) or vice versa (up-flow radial-axial reactor with gas flowing upwards; first zone with prevalently radial flow and second zone with prevalently axial flow).

2. Statement of the Prior Art

The problems affecting synthesis reactors are well known, particularly when it is necessary to use a considerable volume of catalyst (low-pressure and high-capacity ammonia and methanol plants). To contain pressure drops from the catalytic bed, and thus energy consumption, axial flow reactors have become very wide and this limits their capacity and increases their cost (for example, ICI reactors for ammonia and methanol). To overcome this inconvenience, radial flow reactors (for example U.S. Pat. No. 4,181,701, Topsoe) have several catalyst layers with circular crown sections and each layer must be sealed at both ends (sealing baffles). This involves burdensome construction to avoid the problems arising from the expansion of the materials used for the various internal parts of the reactor, and further complications when loading and unloading the catalyst. According to this known technique, the catalyst layers are arranged in a very complex single metal structure (catalyst basket) situated inside the reactor's shell; burdensome equipment is usually required to lift this structure for maintenance and for replacing the catalyst.

On the other hand, the various synthesis loops currently used in ammonia production are all based on the same process scheme, so that the different technologies are fundamentally characterised by reactor design and by the scheme for recovery of heat produced in synthesis. The internal parts of the reactor (cartridge) are designed to minimize gas pressure drops, while ensuring better gas distribution through the catalytic beds and facilitating the introduction of exchangers for exchanging heat between reacted and fresh gas. The design of the reactor must also ensure ease of access for maintenance and for loading and unloading the catalyst. According to the recent low-energy process schemes using low-pressure loops in large reactors, the above-mentioned requirements become even more critical, since larger amounts of recycle gas are involved.

The most widely used reactors are arranged vertically with axial gas flow (Uhde-ICI-Kellogg) or radial gas flow (Topsoe), with the exception of a single horizontal reactor (Kellogg) installed in a large production plant (Japan).

Similarly to the external shell the cartridge, i.e. the internal part of the reactor, is usually made in a single piece, requiring considerable effort at the construction stage and during transport, erection and maintenance, particularly in large production plants. In conventional reactors with shell and cartridge in a single piece gas flow can be either radial or axial; radial gas flow (Lummus, Topsoe, Kellogg; U.S. Pat. Nos. 3,918,918 and 4,181,701, European Patent Application No. 0,007,743-1) seems the most suitable for large reactors in low-pressure plants.

In axial-flow reactors it is imperative to use large-size catalysts in order to contain pressure drops, thus increasing the specific volume of the reactor.

OBJECTS AND SUMMARY OF THE INVENTION

An object of this invention is a reactor free from these drawbacks, having a simple internal structure easily accessible for maintenance and for loading and replacing the catalyst, which will, at the same time, limit pressure drops.

Another object is a reactor, the inner cartridge of which is advantageously formed of a number of stackable modular cartridges.

These and other objects are achieved according to the invention with an axial-radial (or radial-axial) flow reactor for chemical reactions in the gaseous phase with heterogeneous catalysis under pressure (for example, ammonia, methanol etc.), consisting of a vertical cylindrical shell inside which are arranged one or more superimposed layers of granular catalyst, characterised by the fact that the gas flows through each layer in a zone with a prevalently axial flow, and in another zone with a prevalently radial flow, said catalytic zone with prevalently axial flow acting also as gas sealing pad (instead of the known sealing baffle) between catalyst layers.

Preferably each catalyst layer is cylindrical with a circular crown cross-section (hollow internal cylindrical area to permit gas distribution). According to an advantageous feature of the invention, the reactor's inner cartridge is formed of stackable modular cartridges, each cartridge module containing a catalyst layer showing a zone with a prevalently axial gas flow and another zone with a prevalently radial gas flow, said prevalently axial flow zone acting also as sealing pad between one catalyst layer and another.

BRIEF DESCRIPTION OF THE DRAWINGS

The various aspects and advantages of the invention will become more apparent from the detailed description of the preferred embodiments shown by way of illustration (and not of limitation) in the attached drawings.

FIGS. 1-2-3 show down-flow axial-radial reactors.

DESCRIPTION OF THE PREFERRED EMBODIMENTS

Figure 1:
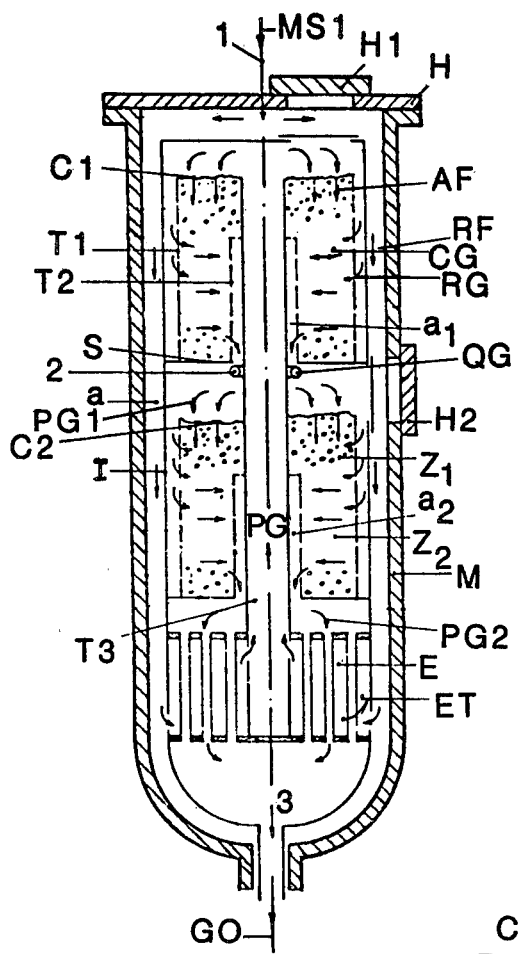
FIG. 1 is a front view of an ammonia synthesis reactor with two catalyst layers, and with an internal exchanger for preheating the fresh gas entering the reactor at the expense of the hot reacted gas leaving the reactor. According to the various installation schemes of the plant, the reactor shown in FIG. 1 may have more than two layers and not contain any internal exchanger, since heat exchange takes place outside the reactor.

According to FIG. 1, the reactor consists of a shell M with lid H, inside which are two catalyst baskets $C_1$ and $C_2$. Each basket consists of a support S and of two cylindrical walls $T_1$ and $T_2$ suitably perforated to allow the gas to be evenly distributed through the catalytic layer.

Internal duct $T_3$, apart from allowing the gas to be directed from the bottom to the top of the reactor, forms the lateral support for the upper zone of each catalyst layer, such zone forming the seal pad which allows even distribution of gas through each layer.

In the particular embodiment shown in FIG. 1 a heat exchanger E will make it possible to preheat the fresh synthesis gas MSI entering the reactor R at the expense of the heat given out by the reacted gas GO. The reactor R is also equipped with internal cartridge I which forms airspace "a" with the internal surface of shell M, and through this airspace runs the cold gas MSI fed to the reactor through 1. Shell M is thus kept at low temperature, avoiding contact with the hot gases being reacted. The two free zones Z at the top of each catalyst basket $C_1$ and $C_2$ permit easy access to the catalytic beds for maintenance and loading and unloading of the catalyst CG through hatches $H_1$ and $H_2$. The reactor works in the following way: the fresh gas MSI fed to the reactor R enters through entrance 1 and flowing along airspace "a" from top to bottom reaches exchanger E in the lower part of the reactor, runs along the exchanger E from bottom to top in the zone outside the exchanger tubes ET and collects inside central tube $T_3$ which conveys the gas PG (preheated in E) to the head of the topmost basket $C_1$ containing the catalyst CG (preferably in granular form).

A part of the gas PG goes through zone $Z_1$ of the first catalytic layer with a prevalently axial flow AF and the remaining gas RG goes through zone $Z_2$ of the same layer with a prevalently radial flow RF.

The hot gas PG reacted in the topmost catalytic basket $C_1$ collects in airspace $a_1$ and after mixing with fresh low temperature quench gas QG, introduced through toroidal distributor 2, collects at the head of the second catalyst basket $C_2$. Analogously to first basket $C_1$, the gas PG+QG runs through the two zones of the catalytic bed ($Z_1$ and $Z_2$), the first ($Z_1$) with a prevalently axial flow and the second ($Z_2$) with a prevalently radial flow.

The volume of the two layers $Z_1$ and $Z_2$, respectively in the two catalyst baskets $C_1$ and $C_2$, and thus the amount of gas going through the layers themselves depend on the characteristics (size and shape) of the catalyst used. In general the volume of the first zone is equal to 5 to 40% of the total volume of the catalyst basket.

The hot gas $PG_2$ reacted in the second catalyst basket $C_2$ collects in airspace $a_2$ and runs through exchanger E from top to bottom inside the exchanger tubes ET giving out heat to the incoming gas. The gas finally leaves the reactor through outlet 3.

Figure 2:
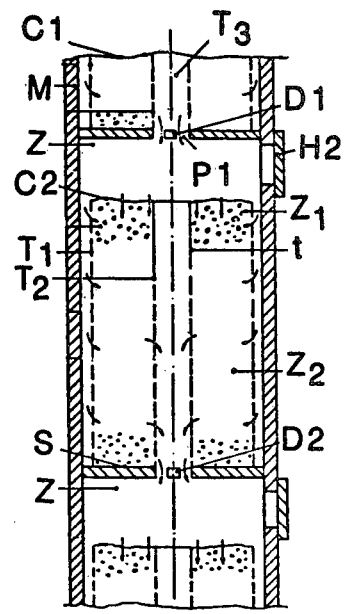
FIG. 2 is a partial front view of a multi-layer reactor for the low-pressure synthesis of methanol, according to the present invention.

With reference to FIG. 2, representing a partial front view of a low pressure methanol reactor, M represents the reactor's shell inside which are arranged the various Cn catalyst baskets (in the partial view in FIG. 2 only basket $C_2$ is fully represented).

It consists of a support S and two cylindrical walls $T_1$ and $T_2$ appropriately perforated to permit the even distribution of gas in the catalytic layer.

According to the major feature of the invention, the upper part t of internal cylindrical wall $T_2$ is solid (not perforated) for a height corresponding to the upper zone ($Z_1$) of the catalytic layer acting as sealing pad, with the prevalently axial flow of gas. The free zone Z above basket $C_2$ permits easy access to the catalytic bed for maintenance and for loading and unloading the catalyst, through hatch $H_2$.

Each catalyst basket Cn (and in particular basket $C_2$) works in the following way:

The gas reacted in the previous basket C1, (only partly shown in FIG. 2) and collected in the empty central space $T_3$ inside the perforated cylindrical wall $T_2$, after mixing with fresh quench gas introduced through distributor $D_1$ in the narrow passage zone $P_1$, where gas mixing is facilitated, feeds the underlying basket $C_2$. A part of the gas goes through upper zone $Z_1$ of the catalytic layer with a prevalently axial flow and the remainder of the gas goes through the underlying zone $Z_2$ of the same layer with a prevalently radial flow.

The reacted gas collects in the empty central space $T_3$ inside the perforated cylindrical wall $T_2$ and feeds the underlying basket, where the above cycle takes place once again.

Figure 3:
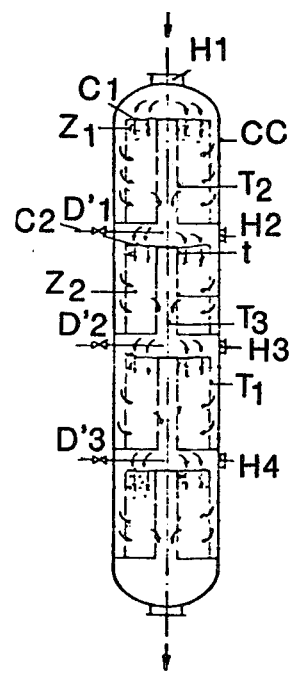
FIG. 3 is a full front view of the reactor in FIG. 2.

FIG. 3 shows a general front view of the methanol reactor of which FIG. 2 shows only one catalytic basket $C_2$.

As shown in FIG. 3, the reactor according to the present invention is built as a cylindrical body with a low diameter/height ratio (very slender equipment, of the filled-column type), with remarkable constructional and operational advantages (simple to construct, low cost, easy maintenance and replacement of the catalyst).

The reactor in FIG. 3 contains four catalyst baskets with three intermediate quenches.

Figure 4:
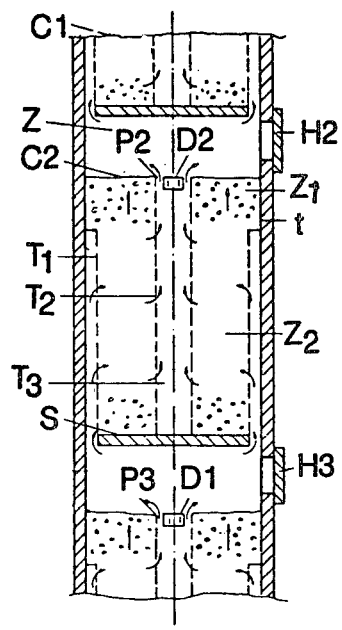
FIGS. 4 and 5 are partial, respectively full front views of the reactor in FIGS. 2 and 3, in which, however, the gas flow is now inverted, i.e. the reactor in FIGS. 4 and 5 is an up-flow reactor, while the reactor in FIGS. 2 and 3 is a down-flow reactor.
Figure 5:
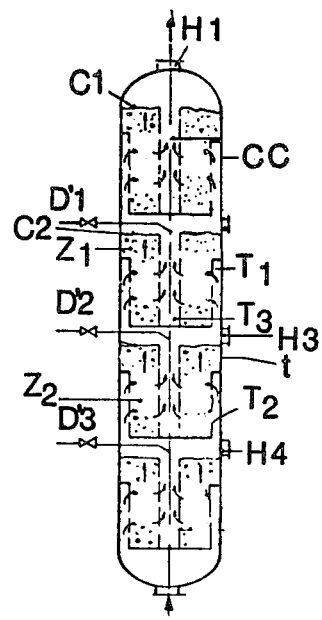

FIGS. 4 and 5 show the same methanol reactor as in FIGS. 2 and 3, with inverted gas flow (up-flow reactor instead of down-flow reactor as in FIGS. 2 and 3).

EXAMPLE 1

A reactor according to the invention for the production of 1000 mt/day of ammonia operating at 250 bar, had two catalytic beds $C_1$ and $C_2$ with the gas in axial-radial flow (down-flow reactor) and with a total volume of 30 m³ of high-yield catalyst formed by small-size particles (1.2–2 mm); in each bed. The volume of catalyst (run through with a prevalently axial flow) is equal to 20% of the volume of the bed, with intermediate quench between the two beds and internal gas-gas exchanger (FIG. 1). Said reactor was built with a cylindrical body having an internal diameter/height ratio of less than 0.08 and with a total pressure loss of less than 2.5 bar. In addition, the catalyst was replaced without removing the internal parts of the reactor in less than two days.

EXAMPLE 2

A reactor for the production of 1500 mt/day of methanol, operating at 150 bar, with four catalytic beds with the gas in axial-radial flow (down-flow reactor) with a total volume of catalyst for methanol synthesis at low pressure equal to 170 m$^3$, in each bed the volume of catalyst run through with a prevalently axial flow being equal to 15% of the volume of the bed, with three intermediate quenches (FIGS. 2 and 3) was built in a single cylindrical body with an internal diameter/height ratio of less than 0.06 and with an overall pressure drop in the reactor of less than 5 bar. Moreover, the catalyst was replaced without removing the internal parts of the reactor in less than three days.

Figure 6:
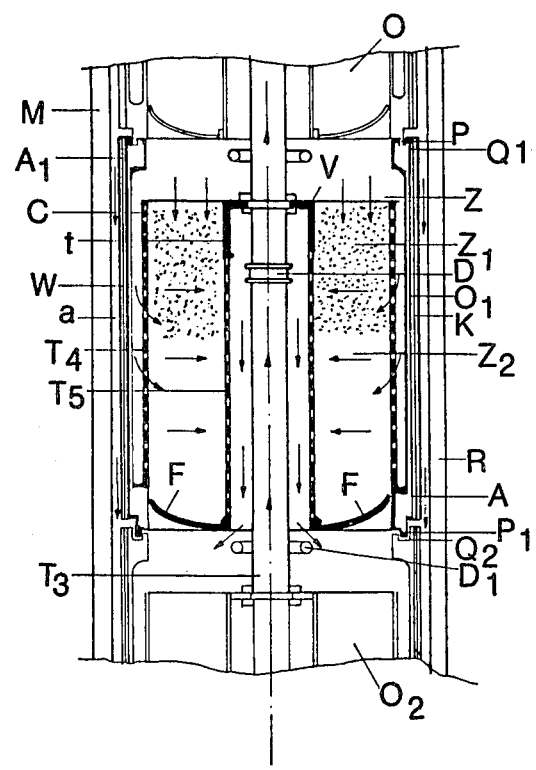
FIGS. 6, 7 and 8 are schematic and partial views of only one cartridge module shown separately, several modules forming the inner cartridge of the above reactors.

Further, it has been found that in the axial-radial mixed-flow reactors according to the invention, the inner cartridge can advantageously consist of modules while the outer shell M and lid H of reactors R remain in a single piece. Said modular cartridge which in the above reactor was in a single piece I, is now formed of individual cartridge modules, $O, O_1, O_2 \ldots O_m \ldots O_{n-1}, O_n, O_1$ of which in FIGS. 6, 7 and 8 module $O_1$ is fully illustrated. As FIG. 6 shows, the individual module $O_1$ is a cylindrical body comprising (going from the outside of the inside): (1) a first solid wall W, i.e. an unperforated wall, which forms air-space (a) with the inside face of shell M; (2) a second wall, $T_4$, perforated; (3) a third wall $T_5$, partly perforated; and (4) a lower bottom E. The outer wall W is longitudinally longer than the two walls $T_1$ and $T_2$ and is so shaped that it has at the top end an annular slot $Q_1$ and at the lower end a projecting tapered end $P_1$. The annular slot $Q_1$ provides support and housing for tapered projecting end P of the upper module O, while projecting part $P_1$ fits into slot $Q_2$ of the lower module $O_2$.

The two perforated walls $T_4$ and $T_5$ form the limits of basket C in which is placed the layer of granular catalyst. $T_4$ and $T_5$ correspond substantially to walls $T_1$ and $T_2$ in FIGS. 1 and 2, with the not negligible difference that while, in FIGS. 1 and 2, tube $T_3$ (conveying internally the gas from the bottom to the top) represented the internal lateral support of the upper zone of each catalytic layer (zone $Z_1$=sealing pad), now the inner wall $T_5$ is always detached from $T_3$ and is fixed to the latter with a connecting ring V which fits into a flange G fixed to $T_3$. Internal wall $T_5$ is not perforated in the upper part t (solid part) so as to create the first zone $Z_1$ with prevalently axial flow and, immediately below, i.e. from the beginning of the perforated part $T_5$, radial flow zone $Z_2$. The central tube $T_3$ is also equipped with an expansion bend D. The bottom F of basket C connects the two walls. $T_4$ and $T_5$ while walls W and $T_4$ are connected to each other by a lower projection or ring A.

The solid external wall W (which forms air-space "a") terminates at the top with a projection or ring $A_1$ in which, as already mentioned, is formed annular slot $Q_1$ into which fits and is held centered lower annular tapered end P. For greater detail, in FIG. 6 is shown the solid wall W lined with a layer of insulating material K which minimizes heat transfer.

Figure 6A:
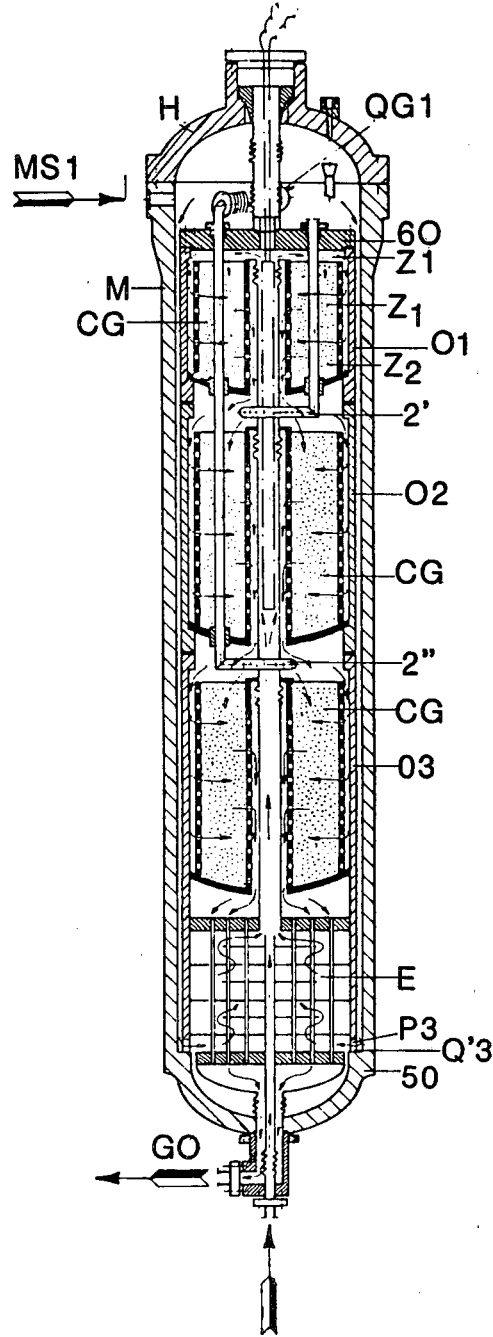
FIGS. 6A and 7A are schematic full front views of the reactors in FIG. 1, respectively 2, with an inner cartridge now formed of several modules (while in FIGS. 1 and 2 the cartridge was intended to consist of a single piece).

FIG. 6A represents schematically a complete reactor (quench) with shell M in a single piece, but with cartridge formed by three modules $O_1, O_2$ and $O_3$; the tapered lower end $P_3$ of $O_3$ fits inside slot $Q'_3$ formed on the lower shoulder 50 of shell M of reactor R. Slot $Q_3$ at the upper end of $O_3$ receives instead the tapered annular base $P_2$ of $O_2$ whose upper slot $Q_2$ receives the base $P_1$ of $O_1$.

The upper end of $O_1$ is coupled to lid 60 which closes the top of the cartridge formed by modules. In FIG. 6A the quench gas inlet is indicated by QGI, the main stream inlet by arrow MSI and the gas outlet by arrow GO; 2′ and 2″ indicate the toroidal distributors of quench gas coming from QGI. In each module is placed granular catalyst CG.

Figure 7A:
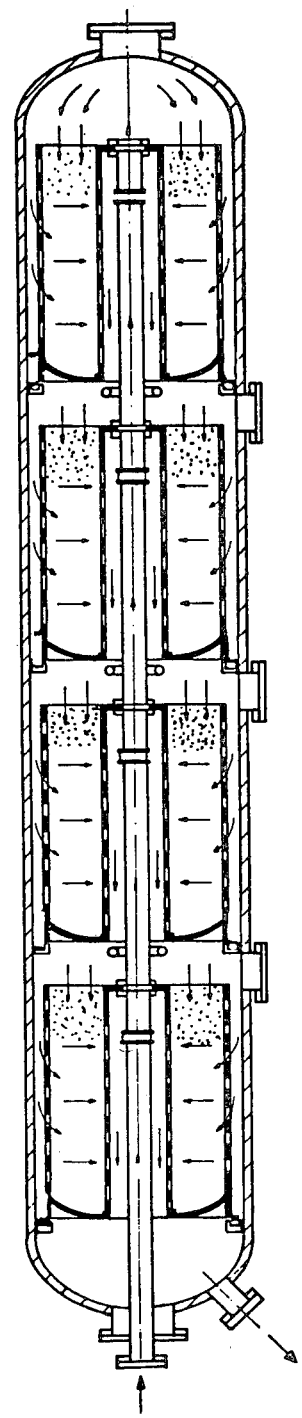
Figure 7:
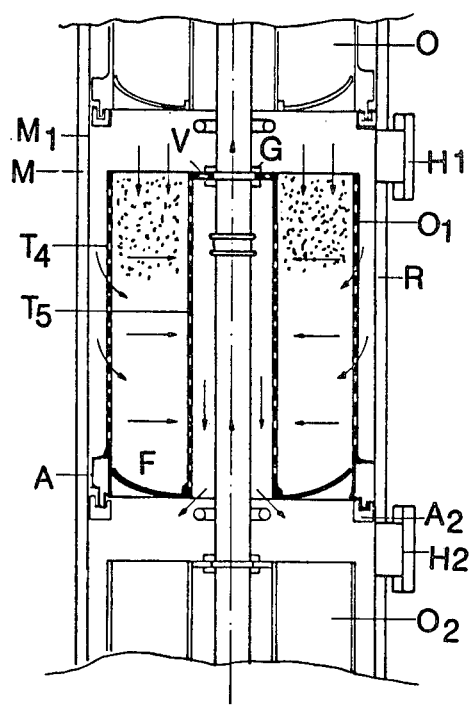

FIG. 7 shows a simplified module $O_1$, forming the cartridge of a low-pressure reactor without air-space for cooling the internal face of the shell M of reactor R in FIG. 7.

In this case the individual modules $O, O_1, O_2$, differ from those in FIGS. 6 and 6A by the absence of outer wall W; the modules still retain a bottom F walls $T_4$ and $T_5$ and lower rings A, but do not have upper rings $A_1$ which are replaced by support rings $A_2$ (respectively $A'_{n-1}$) fixed and protruding from internal wall $M_1$ of shell M which is equipped with manholes $H_1$ and $H_2$ situated at the open upper end of each module $O_1$ for ease of access, for maintenance and loading and unloading of the catalyst.

Figure 8:
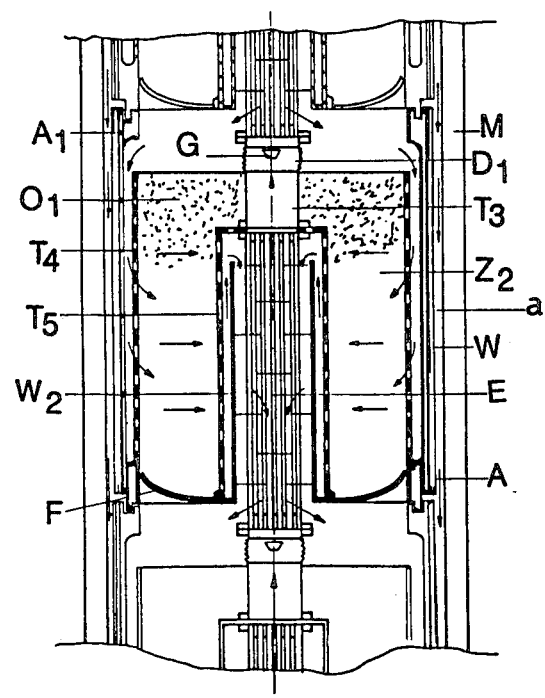

FIG. 8 shows a module in the case of indirect exchange (through heat exchanger and not through quenching by gas mixing) between feed gas and hot gas from the catalytic bed.

In this case module $O_1$, besides the parts described in the case in FIG. 6 includes solid internal wall $W_2$ to convey the hot gas from the catalytic bed $Z_2$ on the outside of the tubes of exchanger E through which run the feed gas tubes. Baffles D on the outside of the tubes help to increase the efficiency of the exchange.

Module $O_1$ is also equipped with connecting duct Y into which is inserted expansion bend D. Inside said duct gas distributor $D_1$ introduces fresh feed gas so that gas temperatures may be more easily controlled.

By using the designs described above it is possible to obtain various types of reactor modules according to the requirements of the synthesis plants, for instance those for ammonia and methanol, operating at various pressure levels (high pressure, medium pressure, low pressure).

It was considered technically very hard to produce a cartridge in several modular units with regard to the problems of sealing between modules which could have generated by-pass gas, with an appreciable reduction in reactor efficiency.

Surprisingly it has been found that thanks to reduced pressure drops due to simplified gas circuits, by-pass gas was practically non-existent even where the various modules were simply connected with slotted seals as shown in the illustrations. A modular cartridge is also advantageous in regard to the problems (caused by technical expansion in the cartridges) which may arise with a single piece.

It is obvious that the invention is not limited to the various embodiments shown in the drawings (supplied by way of illustration) but can be varied in all the ways available to the expert in the Art.

For example, in FIGS. 7 and 7A the gas flow may also be from top to bottom so that the central tube $T_3$ and related flanges G are eliminated and the connecting ring becomes a solid disc.

It is also obvious that the module described in FIG. 8 may be without part (W) which forms an air space as in the module shown in FIG. 7.

The advantages obtained are the following:

(1) less energy consumption owing to reduced pressure drops as a result of simplified gas runs inside the reactor.

(2) minimum investment and maintenance costs. When necessary the individual cartridge modules can be easily replaced.

(3) easy assembly of the modular cartridge and loading and unloading of the catalyst The lighter weight of the individual modules, compared to the weight of the entire conventional cartridge, makes the use of expensive lifting cranes found at plants unnecessary and appreciably reduces transport costs. Monolithic reactor cartridges in one piece usually require expensive metal framing for packing.

(4) Less expensive and more easily constructed cartridge.

The individual modules, in fact, require far less precision in construction than a cartridge in a single piece.

(5) The need for a sealing baffle at the top of each catalyst basket in conventional radial flow reactors showed the further drawback that, owing to the settling of the catalytic layer, the ensuing void between baffle bottom and catalyst upper surface caused considerable gas by-pass. The prevalently axial flow zone $Z_1$ according to the present invention (determined by the unperforated surface $T_5$ of the basket) acts now also as a gas sealing pad, thus permitting the elimination not only of the conventional baffle, but also of the inefficient catalyst top layer needed over the upper end of the catalytic layer to compensate for settling, but which, not taking part in gas conversion, represented an additional wasted cost.

I claim:

1. A reactor for heterogeneous catalytic reactions of gaseous reactants under pressure, comprising:
    a container having an inlet for introduction of said gaseous reactants and an outlet for the efflux of products of said reactions;
    a cartridge having a cylindrically shaped wall placed within said container and communicating with said inlet and said outlet;
    at least two stationary-bed, catalyst-containing baskets supported within said cartridge, each of said baskets including an imperforate bottom section, a cylindrical outer perforated wall, a cylindrical inner concentric perforated wall and an annular opening defined by said inner and outer perforated walls in the upper end of each stationary-bed, catalyst-containing basket, said opening formed in a plane approximately perpendicular to the longitudinal axis of said inner and outer perforated walls, said bottom section and said inner and outer perforated walls cooperating with said cylindrically shaped cartridge wall to form a partially restrictive axial flow means, whereby a portion of said gaseous reactants enters or departs and passes through said annular opening in each of said stationary-bed, catalyst-containing baskets substantially in the axial direction and the remainder of said gaseous reactants enters and passes through the cylindrical outer perforated wall of each of said catalyst-containing baskets substantially in the radial direction.

2. A reactor according to claim 1, wherein said inner wall has perforations only on a lower portion thereof.

3. A reactor according to claim 1, wherein said outer wall has perforations only on a lower portion thereof.

4. A reactor according to claim 1, wherein the upper portion of said inner wall has a smaller diameter than the lower portion thereof.

5. A reactor according to claim 1, wherein said inner wall has perforations only in the lower portion thereof and said lower portion of said inner wall has a larger diameter than the upper portion of said inner wall.

6. A reactor according to claim 1, wherein said outer wall has a larger diameter in the upper portion thereof than in the lower portion of said outer wall.

7. A reactor according to claim 1, wherein said outer wall has perforations only in the lower portion thereof and the upper portion of said outer wall has a larger diameter than the lower portion thereof.

8. A reactor according to claim 1, wherein said partial restrictive axial flow means diverts said gaseous reactants in the axial direction through a portion of each of said at least two catalyst-containing baskets corresponding to about 5 to 40% of the volume of each basket.

9. A reactor according to claim 1, wherein a means for quenching the products of said reactions is placed between each of said at least two catalyst-containing baskets.

10. A reactor according to claim 20, wherein said gaseous quenching means comprises a toroidal distributor.

11. A reactor according to claim 9, wherein said quenching means introduces fresh gaseous reactants.

12. A reactor according to claim 1, wherein the ratio of the internal diameter of said container to the height of the reactor is less than 0.1.

13. A reactor for heterogeneous catalytic reactions of gaseous reactants under pressure, comprising:
    a container having an inlet for introduction of said gaseous reactants and an outlet for the efflux of products of said reactions;
    a cartridge placed within said container and communicating with said inlet and said outlet, said cartridge formed by a plurality of stationary-bed, catalyst-containing modules, each module including an imperforate bottom section which joins a cylindrical outer perforated wall to a concentric perforated inner wall, said inner and outer perforated walls defining an annular opening in the upper end of each stationary-bed, catalyst-containing basket, said opening formed in a plane approximately perpendicular to the longitudinal axis of said inner and outer perforated walls, said bottom section and said inner and outer perforated walls cooperating with an imperforate wall section of said cartridge to form a partially restrictive axial flow means, and a means for securing said modules within said container, whereby a portion of said gaseous reactants enters or departs and passes through said annular opening in each of said stationary-bed, catalyst-containing modules substantially in the axial direction and the remainder of said gaseous reactants enters and passes through the cylindrical outer perforated wall of each of said catalyst-containing modules substantially in the radial direction.

14. A reactor according to claim 13, wherein said inner wall has perforations only on a lower portion thereof.

15. A reactor according to claim 13, wherein said outer wall has perforations only on a lower portion thereof.

16. A reactor according to claim 13, wherein the upper portion of said inner wall has a smaller diameter than the lower portion thereof.

17. A reactor according to claim 13, wherein said inner wall has perforations only in the lower portion thereof and said lower portion of said inner wall has a larger diameter than the upper portion of said inner wall.

18. A reactor according to claim 13, wherein said outer wall has perforations only on a lower portion thereof.

19. A reactor according to claim 13, wherein said outer wall has a larger diameter in the upper portion thereof than in the lower portion of said outer wall.

20. A reactor according to claim 13, wherein said outer wall has perforations only in the lower portion thereof and said upper portion of said outer wall has a larger diameter than the lower portion thereof.

21. A reactor according to claim 13, wherein said partial restrictive axial flow means diverts said gaseous reactants in the axial direction through a portion of each of said at least two catalyst-containing baskets corresponding to about 5 to 40% of the volume of each basket.

22. A reactor according to claim 13, wherein a means for quenching the products of said reactions is placed between each of said at least two catalyst-containing baskets.

23. A reactor according to claim 13, wherein said securing means comprises an inwardly projecting annular ring on the upper edge of said inner wall, said inwardly projecting annular ring engaging a first annular slotted flange mounted on the outer surface of said internal duct and a vertically projecting annular ring engaging a second annular slotted flange secured to the inner surface of said container.

* * * * *